United States Patent [19]
Montanari et al.

[11] Patent Number: 6,063,964
[45] Date of Patent: May 16, 2000

[54] 5-HYDROXYMETHYL-2-AMINOTETRALINS AS CARDIOVASCULAR AGENTS

[75] Inventors: Stefania Montanari; Paolo Cavalleri; Francesco Santangelo, all of Milan; Francesco Marchini, Lodi, all of Italy

[73] Assignee: Zambon Group S.p.A., Vicenza, Italy

[21] Appl. No.: 09/341,673

[22] PCT Filed: Feb. 4, 1998

[86] PCT No.: PCT/EP98/00589

§ 371 Date: Jul. 16, 1999

§ 102(e) Date: Jul. 16, 1999

[87] PCT Pub. No.: WO98/38155

PCT Pub. Date: Sep. 3, 1998

[30] Foreign Application Priority Data

Feb. 26, 1997 [IT] Italy .................. MI97A0414

[51] Int. Cl.[7] .................................. C07C 211/00
[52] U.S. Cl. ............................................. 564/428
[58] Field of Search ............................... 564/428

[56] References Cited

FOREIGN PATENT DOCUMENTS 2 803 582  8/1979  Germany .
9 507 885  3/1995  WIPO .

OTHER PUBLICATIONS

John D. McDermed et al., "Synthesis and Pharmacology of Some 2–Aminotetralins", *Journal of Medicinal Chemistry,* vol. 18, No.4, pp. 362–367, 1975.
Sugihara, H et al, Chem. Pharm. Bull (1978) 26 (2) 394–404.
Beer, Margaret et al. Biochem. Pharmacol (1988) 37(6) 1145–51.
Inatomi N et al. Arzneim–Forsch (1980) 30(2) 276–85.

*Primary Examiner*—Paul J. Killos
*Attorney, Agent, or Firm*—Arent, Fox, Kintner, Plotkin & Kahn

[57] ABSTRACT

Compounds of formula (I) wherein $R_1$ and $R_2$ are independently hydrogen or an optionally branched $C_{1-4}$ alkyl group; the asterisk marks an asymmetric carbon atom; and the pharmaceutically acceptable salts thereof, useful in cardiovascular field, are described.

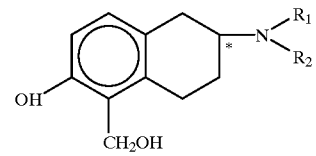

(I)

8 Claims, No Drawings

5-HYDROXYMETHYL-2-AMINOTETRALINS AS CARDIOVASCULAR AGENTS

The present invention relates to compounds active in the cardiovascular field, and specifically to hydroxymethyl derivatives of tetrahydronaphtylamines and to the therapeutical use thereof.

The patent application DE 28 03 582 refers to 2-aminotetralin derivatives optionally substituted in 5-position by a hydroxymethyl group, but none of the exemplified compounds have this specific residue.

This event is clear in view of McDermed, J. D. et al., J. Med. Chem., 1975, 18(4), 362–367 which disclose the synthesis and dopaminergic activity of some 2-aminotetralins, and particularly of 2-(dipropylamino)-1,2,3,4-tetrahydro-5,6-dihydroxy-naphthalene. The 5-hydroxymethyl-2-aminotetralins are excluded from the pharmacological evaluation because it is impossible to synthesise them. Precisely the Authors affirm not to be able to deprotect the hydroxy group in 6-position without decomposing the hydroxymethyl group in 5-position even when protected.

As far as we know, until now no one was able to synthesise 5-hydroxymethyl-6-hydroxy-2-aminotetralins, and consequently to test their pharmacological activity.

Therefore the present invention relates to compounds of formula I

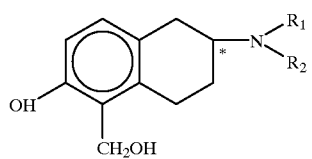

wherein $R_1$ and $R_2$ are independently hydrogen or an optionally branched $C_{1-4}$ alkyl group;

the asterisk marks an asymmetric carbon atom;

and the pharmaceutically acceptable salts thereof.

The compounds of formula I have at least an asymmetric centre marked by an asterisk, and thus may be in form of stereoisomers.

Objects of the present invention are compounds of formula I in form of stereoisonieric mixture so as in form of single stereoisomers.

The compounds of formula I are agonist of the dopaminergic receptors, also orally active. They are therapeutically useful in the cardiovascular field, specifically in the treatment of arterial hypertension, heart and renal failure, in the treatment of peripheral arteriopathies, cerebrovascular insufficiencies, ischemic cardiopathy and arrhythmia, and in the central nervous system, particularly in the treatment of Parkinson's disease, depression and as prolactin inhibitors.

Specific example of alkyl groups are methyl, ethyl, n-propyl, i-propyl, n-butyl, s-butyl and t-butyl, n-propyl being preferred.

Preferred compounds of formula I are the one wherein the carbon atom marked by an asterisk has the S configuration.

Pharmaceutical acceptable salts of the compounds of formula I are those with organic and inorganic acids such as, for example, hydrochloric, hydrobromic, hydroiodic, nitric, sulphuric, phosphoric, acetic, benzoic, maleic, fumaric, succinic, tartaric, citric, aspartic, methansulfonic and 3,7-di-t.butylnaphthalen-1,5-disulfonic acid (dibudinic acid).

The preparation of the compounds of formula I is another object of the present invention in that it has been carried out overcoming a prior art prejudice, i.e. it was impossible to obtain the compounds of formula I and particularly to deprotect the hydroxy group in 6-position while maintaining the hydroxymethyl group in 5-position even when protected, as already said above.

The preparation starts from the naphthylamine of formula II, optionally in form of salt

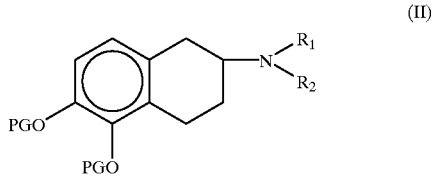

wherein $R_1$ and $R_2$ are as defined above and PG are protective groups suitable for the hydroxy moiety such as benzyl and methyl, which is synthesised, for example, as described in the patent application WO 95/07885. The protective group in 5-position is removed with iodotrimethylsylane. Before this reaction it may be desirable, but not compulsory, to protect the amino group in the case it is primary or secondary, i.e. when at least one of $R_1$ and $R_2$ is hydrogen, with a suitable protecting group such as, for example, trifluoroacetyl in the case of a secondary amine, or phthalimido in the case of a primary amine. It is thereby obtained the compound of formula III

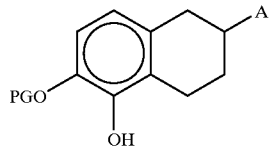

wherein PG is as defined above, and A is a $R_1$-N-$R_2$ group wherein $R_1$ and $R_2$ are as defined above or suitably protected primary or secondary amino group.

At this point of the synthetic route, if it starts from a compound of formula II with a primary or secondary amino group, i.e. a compound of formula II wherein at least one of $R_1$ and $R_2$ is hydrogen, it is possible, if desired, to selectively deprotect such amino group and then react it with a suitable acid or a derivative thereof such as an acyl halide or a mixed anhydride which may be prepared in situ, in an inert solvent in the presence of a base such as an alkali carbonate or hydrogenocarbonate or a tertiary amine, to give an intermediate of formula III wherein $R_1$ and $R_2$ are a $C_{1-4}$ alkyl group. Then the substitution of the hydroxy group in 5-position of the compound of formula III is carried out. Before carrying this reaction out it is necessary to protect the primary or secondary amino group eventually present in the compound of formula III, in the case it was not still modified in this way. Thus the hydroxy group in 5-position is transformed in triflate group by reacting with, for example, N-phenyltrifluoromethansulfonimide or trifluorometansulfonic anhydride, then carbonylated with carbon monoxide in the presence of a transition metal catalyst, preferably, palladium acetate, and of a binding agent such as for example, 1,3-bisdiphenylphosphinopropane, 1,4-bisdiphenylphosphinobutane, to yield a compound of formula IV

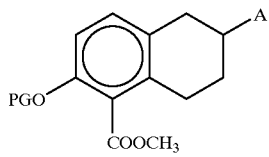

(IV)

wherein PG and A are as defined above.

The compound of formula IV is deprotected on the hydroxy group in 6-position. In the same time or subsequently, it is possible, if desired, to remove the amino protecting group possibly present. The thus obtained compound of formula V

(V)

wherein A is as defined above, undergoes to the reduction of COOCH$_3$ group by a reducing agent such as borane methylsulfide or lithium aluminium hydride or lithium borohydride, to give compounds of formula I. The final products may be still protected on the amino group, and in this case the deprotection of such residue is the last step of the synthetic procedure.

The compounds of formula I in optically active form are obtained by optical separation or using stereospecific or stereoselective methods of synthesis.

The preparation of the salts of the compounds of formula I is carried out by applying conventional methods.

The compounds of formula I are agonist of the dopaminergic receptors $D_1$ and $D_2$ as showed by the in vitro activity tests on receptors $D_1$ and $D_2$ (example 7). But the characteristics conferring a peculiar importance to the compounds of formula I is the surprising bioavailability thereof, higher then the one of other tetralin derivatives, and this is undoubtedly an advantage over the prior art compounds. Actually the higher bioavailability of the compounds of the invention yields higher plasmatic concentration and a greater homogeneity of the effect in different populations of patients.

Therefore the compounds of formula I are particularly suitable for the treatment of cardiovascular diseases, and mainly in the therapy of arterial hypertension, heart and renal failure, in the treatment of peripheral arteriopathies, cerebrovascular insufficiencies, ischemic cardiopathy and arrhythmia, and in the central nervous system, particularly in the treatment of Parkinson's disease, depression and as prolactin inhibitors.

The major characterising feature of the compounds of formula I object of the invention is the oral bioavailability thereof.

Consequently in the practical therapeutic uses the compounds of formula I may be administered both parenterally and enterally differing from dopamine and dopexamine. The therapeutic doses are generally comprised between 1 and 100 mg/day and between 0.5 and 50 mg each oral administration.

Another object of the present invention is a pharmaceutical composition containing a therapeutically effective amount of a compound of formula I or of a pharmaceutically acceptable salt thereof in admixture with a suitable carrier.

The pharmaceutical compositions of the invention may be liquid for the enteral or parenteral administration, and, preferably, solid such as tablets, capsules, granulates, suitable for the oral administration.

The preparation of the pharmaceutical composition of the invention may be carried out according to common techniques.

For better illustrating the present invention the following examples are now provided. The chromatographic purifications are effected on silica gel columns (230–400 mesh). The mass spectra are effected, unless otherwise indicated, under the following conditions: chemical ionization, isobutane, positive ions.

EXAMPLE 1

Preparation of (S)-N-(6-benzyloxy-5-hydroxy-1,2,3,4-tetrahydro-2-naphththyl)-N-propyl-trifluoroacetamide A suspension of N-propyl-5,6-dibenzyloxy-1,2,3,4-tetrahydro-2-naphthylamine hydrochloride (5 g; 11.42 mmoles) and triethylamine (4.2 ml; 28.57 mmoles) in methylene chloride (100 ml), under stirring at room temperature, was dropwise added with a solution of trifluoroacetic anhydride (1.7 ml; 12 mmoles) in methylene chloride (20 ml). After 30 minutes water was added (100 ml). The phases were separated and the organic one was washed first with a solution of 1N hydrochloric acid (100 ml) then with water (100 ml), anhydrified over sodium sulphate and the solvent was evaporated under reduced pressure. The resulting crude was dissolved in chloroform (60 ml) and the solution was dropwise added under stirring at room temperature, with iodotrimethylsylane (2.44 ml; 17.13 mmoles). After 3 hours the reaction mixture was poured into methanol (200 ml) and the solvents were evaporated under reduced pressure. The residue was added with methylene chloride (200 ml) and water (150 ml). The phases were separated and the organic one was washed first with a 5% solution of sodium thiosulfate (150 ml) then with a saturated solution of sodium chloride (150 ml), anhydrified over sodium sulphate and the solvent was evaporated under reduced pressure. The crude thus obtained was purified by silica gel chromatography (eluent: petrolatum:ethyl acetate=8:2).

There were obtained 3.4 g of (S)-N-(6-benzyloxy-5-hydroxy-1,2,3,4-tetrahydro-2-naphthyl)-N-propyl-trifluoroacetamide.

$^1$H-NMR (200 MHz, CDCl$_3$): δ (ppm) 0.91 and 0.92 (2t, 3H); 1.57–2.31 (m, 4H); 2.58–3.39 (m, 6H); 4.02–4.24 (2m, 1H); 5.08 (2s, 2H); 5.73 and 5.76 (2s, 1H); 6.55 and 6.57 (2d, 1H); 6.75 and 6.77 (2d, 1H); 7.29–7.43 (m, 5H).

Mass: 408 (M+H)

EXAMPLE 2

Preparation of (S)-N-propyl-6-benzyloxy-5-hydroxy-1,2,3,4-tetrahydro-2-naphthyl-amine A suspension of (S)-N-(6-benzyloxy-5-hydroxy-1,2,3,4-tetrahydro-2-naphthyl)-N-propyl-trifluoroacetamide (1 g; 2.45 mmoles), prepared as described in example 1, in methanol (10 ml) was added, under stirring at room temperature, with a solution of sodium hydroxide (0.4 g; 9.83 mmoles) in water (0.6 ml). The reaction mixture was refluxed for 3.5 hours, then left at room temperature overnight. After cooling to 0° C. ethyl ether saturated with gaseous hydrochloric acid was added until complete acidification and the solvents were evaporated under reduced pressure. The residue was added with ethyl acetate and a 5% solution of ammonia. The phases were separated and the organic one was washed with water, anhydrified over sodium sulphate and the solvent evaporated under reduced pressure.

There were obtained 740 mg of (S)-N-propyl-6-benzyloxy-5-hydroxy-1,2,3,4-tetrahydro-2-naphthylamine.

$^1$H-NMR (200 MHz, CDCl$_3$): δ (ppm) 0.93 (t, 3H); 1.41–1.67 (m, 3H); 1.98–2.14 (m, 1H); 2.41–3.03 (m, 7H); 5.05 (s, 2H); 6.54 (d, 1H); 6.72 (d, 1H); 7.27–7.41 (m, 5H).

Mass: 312 (M+H)$^-$.

The product was subsequently transformed into the corresponding hydrochloride by dissolution in ethyl acetate saturated of hydrochloric acid and evaporation of the solvent under reduced pressure.

EXAMPLE 3

Preparation of (S)-N,N-dipropyl-6-benzyloxy-5-hydroxy-1,2,3,4-tetrahydro-2-naphthyl-amine A solution of (S)-N-propyl-6-benzyloxy-5-hydroxy-1,2,3,4-tetrahydro-2-naphthyl-amine hydrochloride (1 g; 2.87 mmoles), prepared as described in example 2, and triethylamine (1.3 ml; 9.3 mmoles) in methylene chloride (10 ml) was added, under stirring at room temperature, with propionyl chloride (0.55 ml; 6.3 mmoles). After 2 hours the reaction mixture was poured into water, the phases were separated and the organic one washed first with diluted hydrochloric acid then with a 5% solution of sodium hydrogenocarbonate, anhydrified over sodium sulphate and dried under reduced pressure. The residue was dissolved in anhydrous tetrahydrofuran (10 ml) and the solution was dropwise added, under stirring at room temperature, with borane methylsulfide (1.5 ml; 17.2 mmoles). At the end of the addition the reaction mixture was refluxed for 20 minutes, then the solvent was evaporated under reduced pressure. The residue was added with methanol (12 ml) and 37% hydrochloric acid (6 ml). After 48 hours at room temperature a 5% solution of sodium hydrogenocarbonate was added until totally basic pH and the mixture was evaporated to dryness under reduced pressure. The residue was added with ethyl acetate and water. The phases were separated and the organic one was washed with a saturated solution of sodium chloride, anhydrified over sodium sulphate and dried under reduced pressure. The resulting crude was purified by silica gel chromatography (eluent: methylene chloride:methanol= 95:5).

There were obtained 500 mg of (S)-N,N-dipropyl-6-benzyloxy-5-hydroxy-1,2,3,4-tetrahydro-2-naphthylamine.

$^1$H-NMR (200 MHz, CDCl$_3$): δ (ppm) 0.87 (t, 6H); 1.37–1.66 (m, 5H); 1.98–2.12 (m, 1H); 2.40–3.10 (m, 9H); 5.06 (s, 2H); 5.70 (bs, 1H); 6.57 (d, 1H); 6.73 (d, 1H); 7.28–7.44 (m, 5H).

The product was subsequently transformed into the corresponding hydrochloride by dissolution in ethyl acetate saturated of hydrochloric acid and evaporation of the solvent under reduced pressure.

EXAMPLE 4

Preparation of methyl (S)-2-benzyloxy-6-dipropylamino-5,6,7,8-tetrahydro-1-naftoate A suspension of (S)-N,N-dipropyl-6-benzyloxy-5-hydroxy-1,2,3,4-tetrahydro-2-naphthylamine hydrochloride (530 mg; 1.36 mmoles), prepared as described in example 3, in acetonitrile (15 ml) was added, at room temperature, with potassium carbonate (563 mg; 4.08 mmoles) and, dropwise, with a solution of N-phenyltrifluoro-methansulfonimide (583 mg; 1.63 mmoles) in acetonitrile (5 ml). The reaction mixture was heated to 50° C. for 19 hours, then the solvent was evaporated under reduced pressure. The residue was added with methylene chloride and water. The phases were separated and the organic one was washed with water, anhydrified over sodium sulphate and the solvent evaporated under reduced pressure. The resulting crude was dissolved in dimethylsulfoxide (6 ml) and methanol (2.5 ml). The solution was added, under nitrogen at room temperature, with triethylamine (0.36 ml; 2.62 mmoles), palladium acetate (18 mg; 0.079 mmole) and 1,3-bisdiphenylphosphinopropane (33 mg; 0.079 mmole). The reaction mixture was then heated to 70° C. under CO pressure (9 bar) for 70 hours, and during this period further palladium acetate (9 mg; 0.039 mmole) and 1,3-bisdiphenylphosphinopropane (16 mg; 0.039 mmole) were added in one portion. After cooling to room temperature the mixture was poured into water and methylene chloride. The phases were separated and the organic one was washed with water, anhydrified over sodium sulphate and dried under reduced pressure. The resulting crude was purified by silica gel chromatography (eluent: methylene chloride:methanol:ammonia 30%= 97:3:0.1).

There were obtained 192 mg of methyl (S)-2-benzyloxy-6-dipropylamino-5,6,7,8-tetrahydro-1-naftoate.

$^1$H-NMR (200 MHz, CDCl$_3$): δ (ppm) 0.86 (t, 6H); 1.38–1.70 (m, 5H); 1.95–2.11 (m, 1H); 2.46–3.10 (m, 9H); 3.86 (s, 3H); 5.06 (s, 2H); 6.72 (d, 1H); 7.00 (d, 1H); 7.24–7.39(m, 5H).

Mass (thermospray): 396 (M+H)$^+$.

EXAMPLE 5

Preparation of methyl (S)-6-dipropylamino-2-hydroxy-5,6,7,8-tetrahydro-1-naftoate A solution of methyl (S)-2-benzyloxy-6-dipropylammino-5,6,7,8-tetrahydro-1-naftoate (190 mg; 0.48 mmole), prepared as described in example 4, in ethanol (15 ml) was kept under stirring at room temperature under hydrogen pressure (50 psi) in the presence of 10% Pd/C (50% water) (70 mg) for 8 hours. After filtering off the catalyst the reaction mixture was evaporated to dryness under reduced pressure and the resulting crude was purified by silica gel chromatography (eluent: methylene chloride:methanol=95:5).

There were obtained 84 mg of methyl (S)-6-dipropylamino-2-hydroxy-5,6,7,8-tetrahydro-1-naftoate.

$^1$H-NMR (200 MHz, CDCl$_3$): δ (ppm) 0.87 (t, 6H); 1.36–2.16 (m, 6H); 2.38–3.30 (m, 9H); 3.92 (s, 3H); 6.78 (d, 1H); 7.11 (d, 1H); 10.90 (bs, 1H).

Mass (thermospray): 306 (M+H)$^+$.

EXAMPLE 6

Preparation of (S)-N-dipropyl-6-hydroxy-5-hydroxymetil-1,2,3,4-tetrahydro-2-naphthyl-amine maleate A solution of methyl (S)-6-dipropylammino-2-hydroxy-5,6,7,8-tetrahydro-1-naftoate (84 mg; 0.27 mmole), prepared as described in example 5, in anhydrous tetrahydrofuran (3 ml) was added with borane methylsulfide in 3 subsequent portions (79 ml+79 ml+53 ml; 0.83 mmoles+ 0.83 mmoles+0.56 mmoles) under stirring at room temperature, at a distance of 1.5 hours one from the other. After each addition the reaction mixture was refluxed for 1 hour. After cooling to 5° C. a mixture of acetic acid (2 ml) and water (2 ml) was dropwise added, the reaction mixture was refluxed for further 40 minutes. The residue obtained after evaporation of the solvents under reduced pressure was dissolved in absolute ethanol and the solution was brought to dryness again. The resulting oil was dissolved in a mixture of methylene chloride/ethyl acetate 1:1. After the addition of a solution of maleic acid (32 mg; 0.27 mmole) in ethyl acetate (0.5 ml) and evaporation of the solvent under reduced pressure there were obtained 100 mg of (S)-N,N-dipropyl-6-hydroxy-5-hydroxymethyl-1,2,3,4-tetrahydro-2-naphthylamine maleate.

$^1$H-NMR (200 MHz, D$_2$O): δ (ppm) 0.81 (t, 6H); 1.38–2.20 (m, 6H); 2.58–3.17 (m, 8H); 3.42–3.60 (m, 1H); 4.51 (s, 2H); 6.11 (s, 2H, maleic acid); 6.62 (d, 1H); 6.86 (d, 1H).

Mass (thermospray): 278 (M+H)$^+$.

EXAMPLE 7

Tests of dopaminergic activity on isolated tissues Evaluation of the D$_1$ activity on the rabbit splenic artery (RSA)

Artery rings were prepared according to Semeraro et al., Naunyn. Schnied. Arch. Pharmacol., 1990, 342, 539. These were contracted with U46619 (9,11-dideoxy-11$_\alpha$, 9$_\alpha$-epoxy-methanprostaglandine F$_2$ $_\alpha$) at a submaximal concentration of 0.1M.

The tested compounds were cumulatively administered.

Dopamine was used as reference compound.

The agonistic activity was evaluated at the peak of the effect and expressed as pD$_2$, i.e. -logEC$_{50}$, as shown in Table 1.

Evaluation of the D$_2$ activity in the rabbit ear artery (REA)

Artery rings were prepared following the method described by Steinsland et al., Science, 1978, 443, 199, modified as follows.

Male New Zealand rabbits (weighing 2.5–3 Kg) were sacrificed by a pentobarbital intravenous injection and bled. The central ear artery was cut into 3 mm-rings.

The samples were placed into a 25 ml-bath containing a Krebs solution (mM/l): sodium chloride 118, potassium chloride 4.7, calcium chloride 2.5, magnesium sulphate 1.2, sodium hydrocarbonate 25, potassium biphosphate 1.2, glucose 11.1, balanced with oxygen 95%/carbon dioxide 5% and maintained at 35±1° C. The Krebs solution was added with EDTA (10 μM) to prevent the cathecolamine oxidation, with desipramine (0,1 μM) and corticosterone (30 μM) to stop the neuronal and extraneuronal cathecolamine re-uptake.

The samples were electrically stimulated (10 Hz, 1 msec., 40–80 mA, 500 msec long) at intervals of 5 minutes.

The tested compounds were cumulatively administered.

Dopamine was used as reference compound.

The agonistic activity was evaluated at the peak of the effect and expressed as pD$_2$, i.e. -logEC$_{50}$, as shown in Table 1.

TABLE 1

D$_1$ and D$_2$ activity of the compound of Example 6 and Ref. A determined by the RSA and REA tests respectively expressed as pD$_2$, i.e. -logEC$_{50}$

| | D$_1$ activity (RSA) | D$_2$ activity (REA) |
|---|---|---|
| Dopamine | 6.4 | 7.8 |
| Example 6 | 6.0 | 8.0 |

These data prove that the compounds of formula I of the present invention have a dopaminergic activity comparable to the one of the reference compounds, but have the advantage of being orally absorbed and very well bioavailable over it.

What is claimed is:

1. A compound of formula I

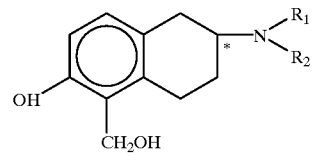

(I)

wherein R$_1$ and R$_2$ are independently hydrogen or an optionally branched C$_{1-4}$ alkyl group;
the asterisk marks an asymmetric carbon atom;
and the pharmaceutically acceptable salts thereof.

2. A compound according to claim 1 wherein the carbon atom marked by an asterisk has the S configuration.

3. Process for preparing a compound of formula I

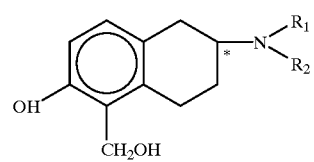

(I)

wherein R$_1$ and R$_2$ are independently hydrogen or an optionally branched C$_{1-4}$ alkyl group; the asterisk marks an asymmetric carbon atom; and the pharmaceutically acceptable salts thereof; wherein an intermediate of formula II

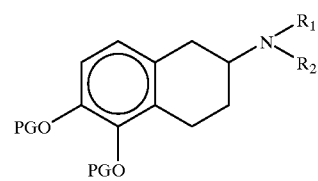

(II)

wherein R$_1$ and R$_2$ are as defined above and PG are protecting groups for the hydroxy moiety such as benzyl and methyl, is reacted with iodotrimethylsilane to remove the protecting group in 5-position, such reaction being optionally effected on a compound of formula II wherein the amino moiety was suitably protected with a protecting group; thereby obtaining a compound of formula III

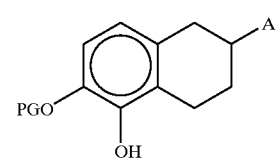

(III)

wherein PG is as defined above, and A is a R$_1$-N-R$_2$ group wherein R$_1$ and R$_2$ are as defined above or a suitably protected primary or secondary amino group which optionally undergoes a deprotection and dialkylation reaction of the amino moiety, and which subsequently but not before having suitably protected the primary or secondary amino group if present, is reacted with an agent capable of transforming the hydroxy group in 5-position into a triflate group, and then undergoes a substitution reaction with carbon monoxide catalysed by a transition metal in the presence of a binding agent, to yield a compound of formula IV

(IV)

wherein PG and A are as defined above; and such compound is subsequently deprotected on the hydroxy moiety in 6-position to yield a compound of formula V

(V)

wherein A is as defined above, which is reduced on the COOCH$_3$ group by a reducing agent to give the compounds of formula I; and this process being characterised in that the final cleavage of the protection at the amino group may be effected both in the same time and subsequently to the cleavage of the protecting group in 6-position and subsequently to the reduction of the COOCH$_3$ group.

4. A process according to claim 3 wherein the agent capable of transforming the hydroxy group in 5-position into a triflate group is selected from the group consisting of N-phenyltrifluoromethansulfonamide and trifluoromethansulfonic anhydride.

5. A process according to claim 3 wherein the substitution of the hydroxy group in 5-position is catalysed by palladium acetate.

6. A process according to claim 3 wherein the binding agent used in the substitution of the hydroxy group in 5-position is selected from the group consisting of 1,3-bisdiphenylphosphinopropane and 1,4-bisdiphenyiphosphinobutane.

7. A pharmaceutical composition containing a therapeutically effective amount of a compound according to claim 1 in admixture with a suitable carrier.

8. A pharmaceutical composition according to claim 7 for the treatment of cardiovascular diseases.

* * * * *